(12) United States Patent
Saito et al.

(10) Patent No.: US 7,001,730 B2
(45) Date of Patent: Feb. 21, 2006

(54) IMMUNOLOGICAL ANALYZING APPARATUS AND IMMUNOLOGICAL ANALYZING METHOD

(75) Inventors: Michihiro Saito, Kashiwa (JP); Kazuhiro Tanaka, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 700 days.

(21) Appl. No.: 10/092,914

(22) Filed: Mar. 8, 2002

(65) Prior Publication Data

US 2002/0182640 A1 Dec. 5, 2002

(30) Foreign Application Priority Data

Apr. 10, 2001 (JP) .............................. 2001-110745

(51) Int. Cl.
*G01N 33/53* (2006.01)
*G01N 21/01* (2006.01)
*G01N 35/02* (2006.01)
*G01N 35/10* (2006.01)

(52) U.S. Cl. ........................... 435/7.1; 436/47; 436/50; 422/67

(58) Field of Classification Search .................. 422/67; 436/50, 47; 435/7.1
See application file for complete search history.

(56) References Cited

FOREIGN PATENT DOCUMENTS

WO   WO 93/20444   * 10/2005

* cited by examiner

*Primary Examiner*—Long V. Le
*Assistant Examiner*—Shafiqul Haq
(74) *Attorney, Agent, or Firm*—Mattingly, Stanger, Malur & Brundidge, P.C.

(57) ABSTRACT

An immunological analyzing apparatus and method using fine particles bonded with an antigen or an antibody are provided which are capable of obtaining a good analysis result with preferable reproducibility with no effect of carry-over.

The immunological apparatus includes plural reagent vessels for containing plural kinds of liquid reagents in which fine particles bonded with an antigen or an antibody are suspended, a stirring vessel for stirring the liquid reagent, a probe for dispensing the liquid reagent, a reaction vessel for mixing and reacting the liquid reagent and a specimen, a measuring device for measuring the reaction in the reaction vessel, and a mechanism for determining as to whether or not the liquid reagent in the reagent vessel is to be stirred prior to dispensing of the liquid reagent in the reagent vessel to the reaction vessel, based on the information regarding the predetermined stirring time interval and the information regarding the carry-over between each of plural kinds of liquid reagents.

5 Claims, 5 Drawing Sheets

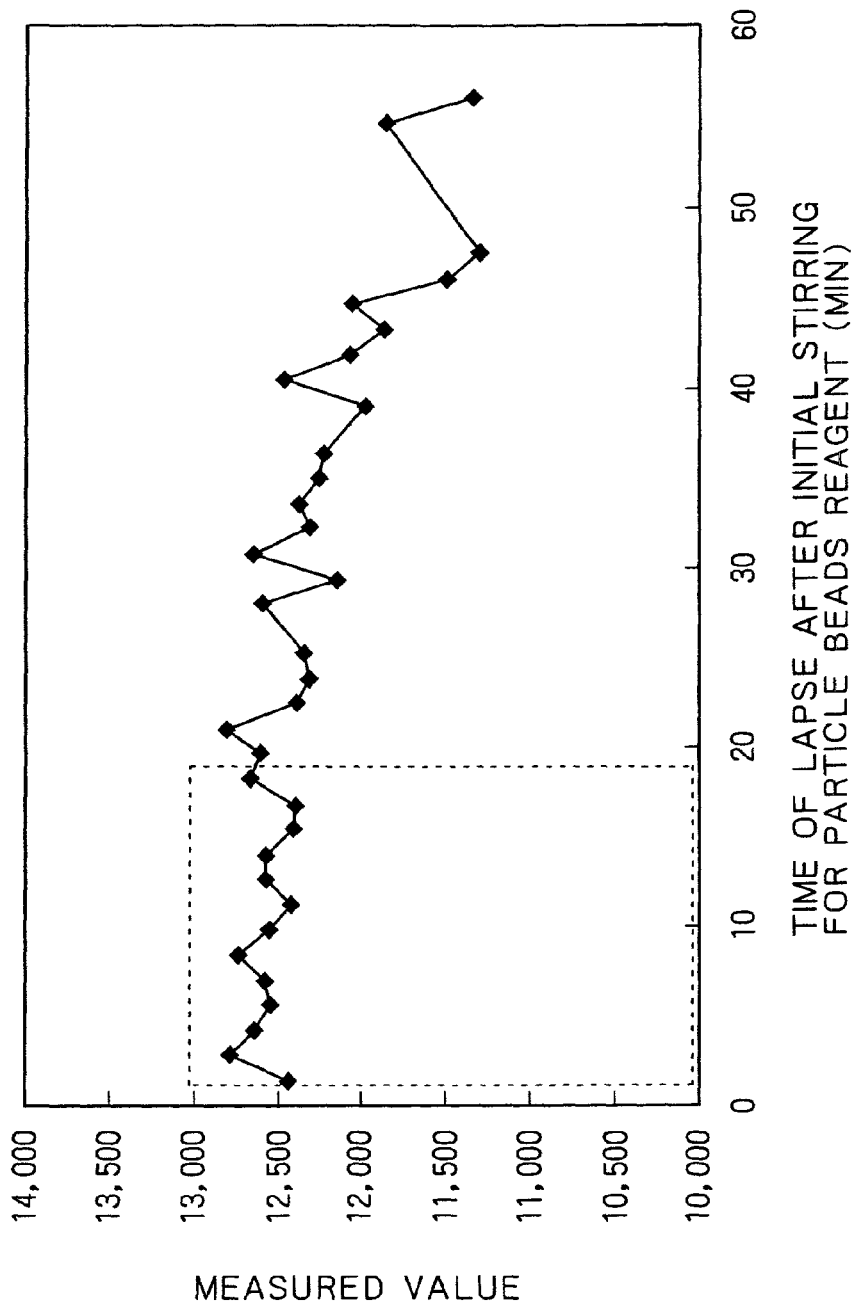

————————————————————————————→ TIME ELAPSED

IMMUNOLOGICAL ANALYZING APPARATUS AND IMMUNOLOGICAL ANALYZING METHOD

BACKGROUND OF THE INVENTION

The present invention relates to an immunological analyzing apparatus and analyzing method using a liquid reagent in which particles (bead particles) bonded with a antigen or antibody are suspended and, more in particular, it relates to an immunological analyzer having a control mechanism for a stirring mechanism that stirs a liquid regent prior to the dispensing operation of the liquid reagent to a reaction vessel, as well as immunological analysis method.

In a heterogeneous immunological analyzing method, slide glass, micro chip, silicious sand such as kaolin, microplate, for example, of 96 wells, plastic beads, polypropylene beads, polycarbonate beads, latex beads, gelatin beads or magnetic beads are used as a solid phase body, and final reaction products are formed on the surface thereof. The final reaction products are bonded with enzyme such as peroxidaze, alkali phosphatase and galactosidase, light emitting substance such as acrydium ester or ruthenium, fluorescent substance such as fluororescein or rhodamine, antibody, antigen or avidin labeled with rare earth coloring substance such as europium. Coloration, light emission, fluorescence or phosphorescence is observed by adding a substrate, a light emitting liquid or a coloring liquid to a labeled body and, if necessary, changing pH, applying voltage or controlling the temperature to an optimal condition. By measuring them, presence or absence of an aimed object and the amount of the object to be analyzed in the specimen can be estimated.

The solid phase body is used as it is, or coated with a substance that concerns the formation of final reaction products such as an antibody, Fab, Fc, antigen, avidin, biotin or protein A, or a substance that inhibits a non-specific reaction not based on the antigen-antibody reaction irrespective of the formation of the final reaction products including the object to be analyzed.

Among the solid phase bodies, particulate or spherical solid phase body is maintained as it is as a dried product of the solid phase body or being suspended in a preservation liquid, diluent or buffer solution such as dispersion solution. Among them, particle beads suspended in the preservation solution, diluent or buffer solution may sometime float or precipitate when they are not stirred due to the difference in the specific gravity between the beads and the liquid. Then, it is ordinary to stir the particle beads before the dispensing operation to the reaction vessel upon measurement so that the particles are uniformly suspended in the buffer solution. If they are not suspended homogeneously, the result of analysis varies and no exact analysis can be attained.

Japanese Patent Laid-Open No. Hei 4-47266 discloses a technique of setting a standard stirring interval and compulsorily stirring the liquid reagent based on the interval time in order to dispense the reagent in a state where the fine particles suspended in the liquid reagent are uniformly dispersed.

In a case where a stirring rod or a stirrer is put in a buffer to stir the liquid by the rotation of the stirring rod or the stirrer, since a portion thereof is immersed in the particle beads reagent upon stirring, contamination (reagent carry-over) may possibly occur between reagents different from each other by way of the stirring rod or the stirrer. The reagent carry-over also worsens the reproducibility of the result of analysis.

However, the stirring method disclosed in Japanese Patent Laid-Open No. Hei 4-47266 takes a notice only on the standard interval for uniform dispersion of micro particles but no consideration has been taken for the carry-over.

An object of this invention is to provide an immunological analysis apparatus and analysis method using a liquid reagent in which micro particles bonded with an antigen or antibody are suspended and which can provide high reproducibility for the result of analysis.

SUMMARY OF THE INVENTION

This invention provides an automatic analyzing apparatus and method using particle beads as a reaction solid phase, having a selection mechanism for determining as to whether or not a vessel containing the particle beads is to be stirred prior to dispensing of the particle beads to a reaction vessel, in which stirring for a vessel containing a certain kind of particle beads is not conducted, stirring for a vessel containing another kind of particle beads is conducted previously, and stirring for vessels containing particle beads are conducted in a sequence different from the sequence of measurement, and the stirring is not conducted just before the dispensing of the particle beads to the reaction vessel based on the information regarding presence or absence or extent of carry-over between reagents of particle beads liquids by way of a stirring rod or information regarding the order of analysis items, while it is ordinary to stir vessels containing plural kinds of particle beads for a certain period upon measurement of plural analysis items in one identical run in view of measuring operation only for a single analysis item and, as a result, continuous measurement is conducted without decreasing the number of analytical processing per time and without carry-over by way of a stirring rod or a stirrer.

This invention provides an automatic analyzing apparatus and method using particle beads as a reaction solid phase, having a selection mechanism for determining as to whether or not a vessel containing the particle beads is to be stirred prior to dispensing of the particle beads to a reaction vessel, in which stirring for a vessel containing a certain kind of particle beads is conducted, stirring for a vessel containing another kind of particle beads is not conducted previously based on the information regarding analysis items, while it is ordinary to stir vessels containing plural kinds of particle beads for a certain period upon measurement of plural analysis items in one identical run in view of measuring operation only for a single analysis item and, as a result, continuous measurement is conducted without decreasing the number of analytical processing per time.

DESCRIPTION OF THE ACCOMPANYING DRAWINGS

FIG. 1 is a graph shows that analysis is conducted preferably for a certain period of time with no further stirring after the stirring a particle beads reagent, in which axis x represents a time (min) from the stirring of particle beads in an ecuresis TSH reagent pack to suction for dispensing into a reaction vessel and axis y indicates a measured amount of signals with the measured values for each data being plotted and connected by a line;

FIG. 5 is a diagram illustrating the measuring sequence of items to be analyzed.

DETAILED DESCRIPTION OF PREFERRED EMBODIMENT

[Embodiment 1]

Figure 2A:
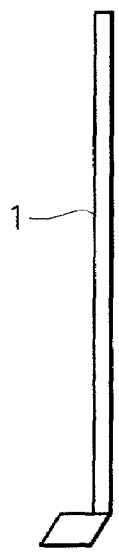
FIG. 2 shows an example of a shape of a stirring rod 1 (FIG. 2–1) and an example of a particle beads reagent bottle stirring device (FIG. 2—2)

Avidin coated particle beads contained in thyroid-stimulating hormone test reagent in an ecuresis TSH reagent pack (manufactured by ROCHE DIAGNOSTICS GMBH) were used and it was observed whether or how was fluctuations in the measured values in a case where beads were not stirred. After being stirred for once by a beads stirrer at first, the particle beads were sucked and discharged not undergoing stirring by a beads stirrer to and from a reaction vessel on every 84 sec and mixed with R1 and R2 reagents and, further, with a predetermined amount of TSH antibody solution and then incubated. Then, the particle beads were cleaned with cleaning water and the amount of light emission was measured by a detector. Measurement was conducted by using an automatic immunological analyzing apparatus under development by the applicants' company.

The time (min) from the stirring to suction of the particle beads in the ecuresis TSH reagent pack for dispensing into the reaction vessel was taken on the axis x and the amount of measured signals was taken on the axis y and the measured values for each data were plotted.

FIG. 1 shows the result. From the result, it was found that the measured values for the beads in the reagent pack did not fluctuate remarkably without undergoing stirring for about 15 min compared with a case of undergoing stirring, and that measurement could be conducted with no effect on the result of the analysis even in a case where particle beads were sucked by several times by merely conducting stirring once on every 15 min.

Since the stirring time interval that gives no effect on the result of the analysis depends on physical property values such as the size of the particle beads or the viscosity of the liquid reagent in which the particle beads are suspended, a standard stirring time interval is previously determined experimentally on every different liquid specimens and recorded as information regarding the stirring time interval.

[Embodiment 2]

An example of the algorithm upon measurement is shown.

(a) Example for Reagent Stirring Procedure for Avoiding Carry-Over

When items A, B, C and D of immunological analysis are analyzed in accordance with a rule or at random, the particle beads reagents A, B, C and D contained in corresponding reagent packs are stirred respectively prior to dispensing them to the reaction vessel. In this case, if the possibility is suggested that carry-over of the particle beads reagent from the particle beads reagent C to D gives an effect on the measured value for the analysis item D or on the diagnostic judgement based thereon, it is possible to select that stirring for the particle beads reagent D subsequent to the particle beads reagent C is not performed. The information on the reagent carry-over may be provided by a reagent manufacturer if it occurs for reagents supplied from one identical reagent manufacturer. Further, it may also be confirmed by actual measurement. Such information is recorded as the information regarding the reagent carry-over.

That is, in a case where the analysis items A, B, C and D are measured in the following sequence:

| 1 | 2 | 3 | 4 | 5 | 6 | 7 | 8 | 9 | 10 | 11 |
|---|---|---|---|---|---|---|---|---|----|----|
| A | B | C | B | D | A | A | C | D | B  | A  | and the particle beads reagents A, B, C and D are dispensed from each one of the bead particle reagent bottles by a reagent dispensing probe, the fifth particle beads reagent D is stirred since it is stirred subsequent to stirring for the particle beads reagent B. However, since the ninth particle beads reagent D is to be stirred subsequent to the particle beads reagent C which may possibly result carry-over, the particle beads reagent D is dispensed without stirring. The particle beads reagent D has already been put to fifth stirring. If it is within a period causing no fluctuation in the measured values when left as it is after stirring as a result of study, for example, according to Embodiment 1, ninth stirring can be saved and, desirably, is not to be conducted considering a possible worry of carry-over. For example, within 5 min, measurement is conducted with no fluctuation in the analyzed value even without stirring of the particle beads. Thus, stirring of the particles beads reagents D before the ninth dispensing can be saved so long as it is within five min after the fifth stirring up to the ninth dispensing of the reagent.

(b) Example for Reagent Stirring Operation in a Case of Intending to Stir Plural Particle Beads Liquids in Identical Period When immunological analysis items E, F, G and H are analyzed in accordance with a rule or at random, the particle beads reagents E, F, G, and H contained in the corresponding reagent packs are stirred respectively prior to dispensing thereof to the reaction vessel.

In a case where it is necessary to stir plural kinds of beads reagents, in an apparatus where only single stirring is conducted in a single period, if the possibility is not suggested that the measured value or the diagnostic judgement based thereon may undergo the effects of the time from the stirring of a particle beads reagent to the dispensing of the reagent to the reaction vessel, it is possible to select that stirring for the particle beads reagent is not conducted or that stirring can be conducted while adapting the sequence of stirring or the timing of stirring to actual analysis.

That is, when analysis for the immunological analysis items E, F, G and H are conducted within the following reaction times and beads are stirred at character M:

E; M--------------------------------

F; ---------M-----------------------

G; M--------------------------------

H; ---------M-----------------------

(M represents the timing for stirring the particle beads reagent), the analysis items E, F, G, H are assumed to be analyzed in the sequence described in FIG. 5.

In a case where the stirring for each of the particle beads reagents is conducted upon continuous measurement, timings for stirring the particle beads reagent overlap and only one stirring is conducted at a determined timing. When it is intended to conduct all the stirring, this may displace the stirring time and, accordingly, result in lowering in throughput. For conducting measurement without lowering the throughput, it is necessary not to conduct stirring except for one at a determined timing.

In the example, stirring for particle beads overlaps between the third analysis item F and the fifth analysis item E and stirring is not conducted for one of them, or is conducted for one of them prior to the stirring time. The fifth particle beads reagent E has already been put to stirring at the first time and it can be selected not to conduct stirring if it is within a period from the first not causing fluctuations in the measured value even when left after stirring as a result of study, for example, according to Embodiment 1 without further stirring the particle beads reagent. Further, the time for stirring one of the third particle reagent F or the fifth particle beads reagent E may be preceded and stirring can be conducted in vacant time after the second particle beads reagent G and the third or the fifth particle beads reagent. In the same manner, upon analysis for the eighth item H and the analysis for the tenth item G, stirring for one of them may not be conducted or the stirring time may be displaced.

(c) Example for the Reagent Stirring Operation for Avoiding the Use of a Stirring Rod Cleaning Liquid.

When the immunological analysis items I and J are analyzed in accordance with a rule or at random, the particle beads reagents I and J contained in the corresponding reagent packs are stirred respectively prior to the dispensing them to reaction vessel. In this case, the following matters are taken into consideration and it can be selected not to conduct stirring if it is within the period not giving effects on the measured value even when the particle beads reagent is not stirred.

(1) To avoid the use of a solution used for cleaning a portion of the stirring rod or the stirrer immersed in particle beads reagent, and avoid the use of water and electric power thereof.

(2) To avoid dilution of reagent by mixing of the deposited cleaning liquid after cleaning the stirring rod or a portion thereof immersed in the particle beads reagent upon stirring with the particle beads reagent to be stirred next.

(3) To avoid unnecessary scattering of particle beads reagent attendant the stirring operation, formation of aerosol, or bubbling on or inside the liquid.

That is, in a case where the analysis items I and J are measured in the following sequence:

| 1 | 2 | 3 | 4 | 5 | 6 | 7 | 8 | 9 | 10 | 11 |
|---|---|---|---|---|---|---|---|---|----|----|
| I | I | J | J | J | J | I | J | I | J  | I  | and the particle beads reagents I, J are dispensed from each one or a plurality of particle beads reagent bottles by a reagent dispensing probe, the first particle beads reagent I and the third particle beads reagent J are stirred. In the particle beads reagents I, J stirred subsequent to the stirring for them, stirring can be saved within a period not causing fluctuation in the measured value even when left after stirring as a result of study, for example, according to Embodiment 1.

In each of the examples, for the analysis items A to J, the reagent packs including the particle beads regents are disposed each by one set on one identical apparatus. When plural reagent packs are used for one analysis item, the particle beads reagent in each of the reagent packs undergoes stirring upon initial dispensing and, subsequently, stirring can be saved within a time not causing fluctuations in the measured values even left after stirring as a result of study according to Embodiment 1, for example.

The immunological analysis items, i.e., analysis items A to J are those inspection analysis items such as thyroid-stimulating hormone, thyroxin, free thyroxin, triiodothyronine, carcino embryonic antigen human chorionic gonadotropin, embroyonal carcino antigen, gravida urofollitropin, troponin T, hepatitis B surface antigen, anti-hepatitis B surface antigen-antibody or other trace amount substances in bloods, serum, plasma, urea, spinal fluid and other body floods of animals including human.

[Embodiment 3]

An example of the shape of a unit regarding the analyzes and an example of the operation thereof are shown.

Figure 2B:
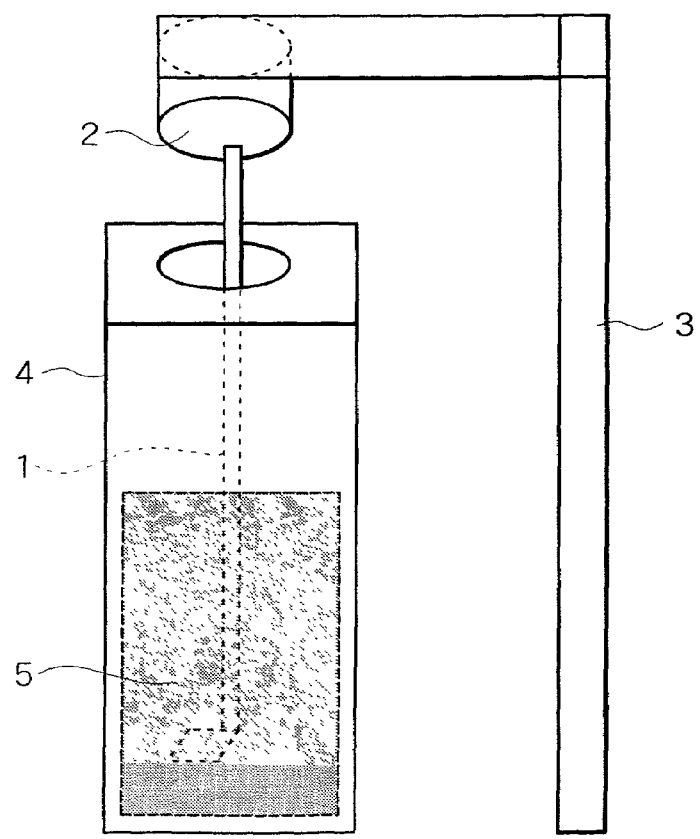

(a) Example of the shape of a stirring rod 1 (refer to FIG. 2–1)

An example of a stirring rod 1 used for stirring particle beads reagent 5 is shown.

(b) Example of a stirring device for bead particles reagent bottle (refer to FIG. 2—2)

An example of a device for stirring beads reagent bottle is shown. A stirring rod 1 is connected with a motor 2 and the particle beads reagent 5 in a reagent bottle 4 is stirred by rotation of the rod. A support rod 3 holds the motor 2 and the stirring rod 1 that rotates and moves vertically to stir the reagent and clean the stirring rod 1.

[Embodiment 4]

Figure 3:
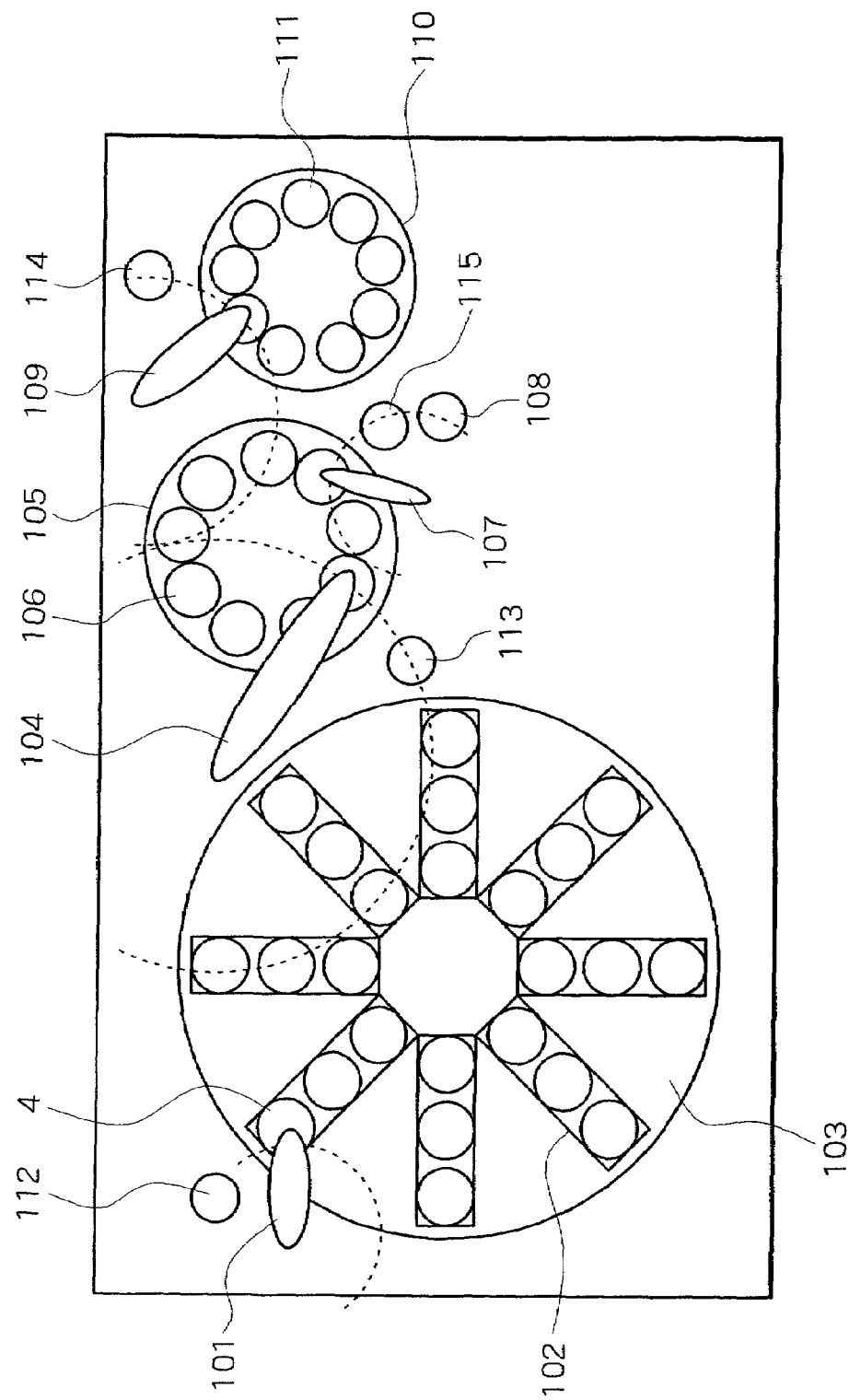
FIG. 3 illustrates an analyzing method using an immunological analyzing apparatus.

With reference to FIG. 3, a constitutional example of an immunological analysis unit is to be described. A plurality of reagent vessels 102 each containing a reagent liquid corresponding to an analysis item that can be analyzed by an immunological analyzer are arranged on a rotary reagent disk 103.

A plurality of specimens 111 are arranged on a rotary specimen disk 110.

A reaction disk 105 kept in a thermostable state can rotate and has plural reaction positions along the circumference on the reaction disk 105, in which reaction vessels 106 are contained. The reaction disk 105 transfers a reaction vessel 106 by rotational operation to a specimen discharging position, a reagent adding position and a reaction solution sucking position.

A reagent dispensing pipetter 104 can move from a position above the reagent sucking position on the reagent disk 103 to a position above the reagent adding position and can also move vertically at each of the positions. A particle beads reagent bottle stirring device 101 can move to a position above the reagent bottle 4 and also can move vertically.

The specimen dispensing pipetter 109 can move horizontally from a position above the specimen sucking position to a position above the specimen discharge position and can also move vertically at each of the positions.

A sipper 107 can move to a position above the reaction solution sucking position and also moves vertically. Further the sipper 107 has a function of feeding the reaction solution by way of a tube to a detection unit.

Each of the reagent dispensing probe, particle beads reagent stirring rod and the specimen dispensing probe can move respectively to the position above each of the corresponding cleaning positions 113, 112 and 114 and also can move vertically at each of the positions. At this position, each stirring rod or probe is cleaned with the cleaning solution.

Then, processing flow in the immunological analysis unit is to be explained. The reagent dispensing pipetter 104 moves the probe to a position above the reagent sucking position, descends into the reagent vessel 102 on the reagent disk 103 and sucks a predetermined amount of a reagent. After the suction of the reagent, the probe ascends and moves to a reagent discharging position. Then, the probe is lowered to discharge the sucked and held reagent into the reaction vessel 106. After discharging the reagent, it moves to a reagent dispensing probe cleaning position 113 to clean the probe. Prior to the suction of the particle beads, the stirring rod of the particle beads reagent bottle stirring device 101 moves to a position above the reagent bottle 4 and descends into the bottle. The stirring rod conducts stirring for the particle beads reagent in the reagent bottle 4 for a predetermined period of time by the rotation of the motor. After stirring, the stirring rod moves to the particle beads reagent stirring rod cleaning position 112 and undergoes cleaning.

The specimen dispensing pipetter 109 moves the probe to a position above the specimen sucking position and descends into the specimen 111 on the specimen disk 110 and sucks a predetermined amount of the specimen. After the suction of the specimen, the probe ascends and moves to the specimen discharging position. Then, it lowers the probe to discharge the sucked and held specimen into the reaction vessel 106. After discharging the specimen, it moves to the specimen dispensing probe cleaning position 114 to conduct cleaning of the probe.

After lapse of a predetermined time required for the reaction, the reaction disk 105 transports the reaction vessel 106 to the reaction solution sucking position. The sipper 107 sucks the reaction solution through a nozzle to the detection unit at the reaction solution sucking position. After sucking the reaction solution, the sipper 107 moves the nozzle to the buffer solution sucking position 115 and sucks a buffer solution. The sucked buffer solution and the reaction solution are sent through a tube to a flow cell in the detection unit and analysis is conducted. Then, the sipper 107 moves the nozzle to the cleaning position 108, sucks a solution for cleaning the nozzle and the flow cell and cleans the inside of the nozzle and the flow cell by the cleaning solution.

[Embodiment 5]

Figure 4:
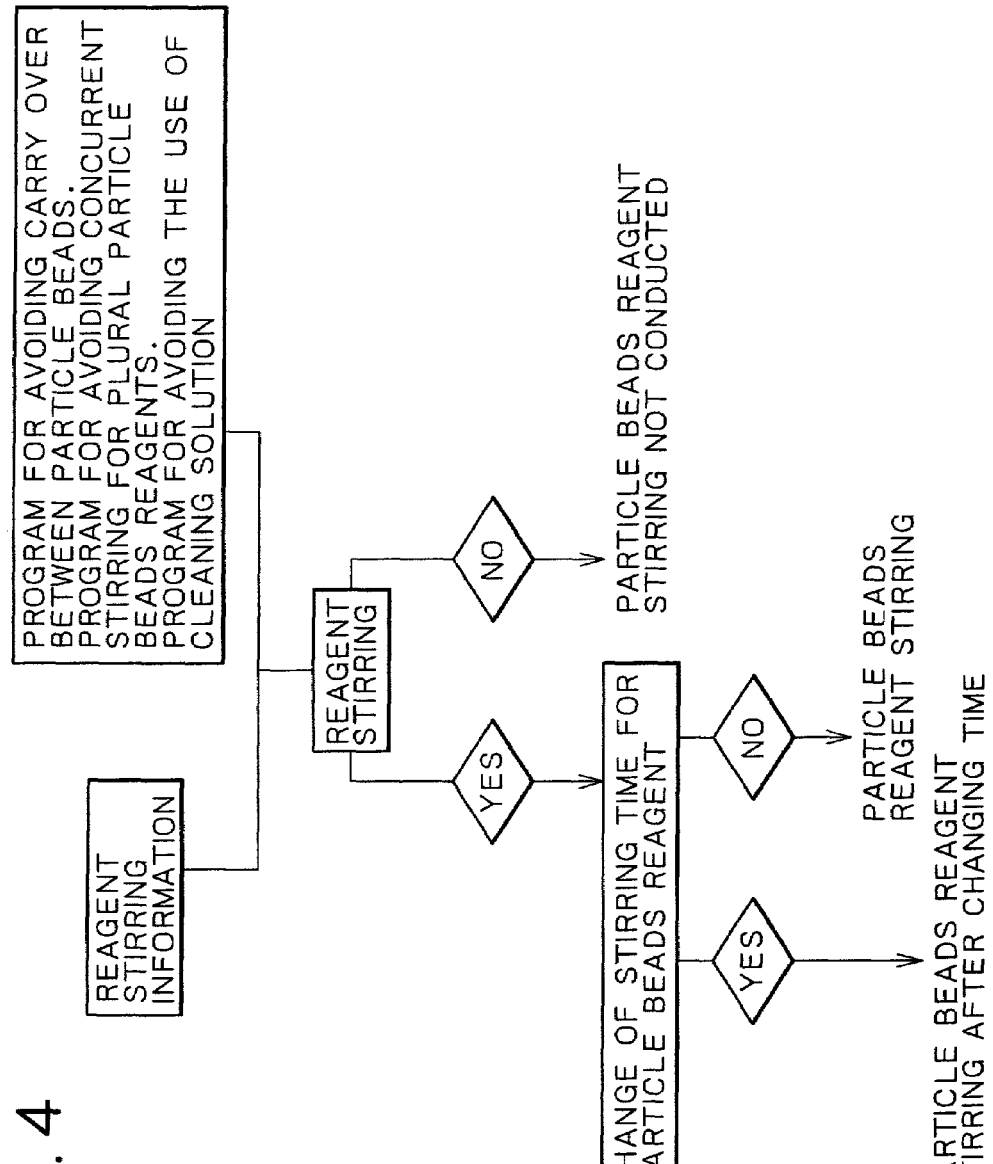
FIG. 4 shows an example of a flow chart upon stirring particle beads reagent in an apparatus.

An example of a flow chart of the apparatus upon stirring the particle beads reagent is shown (refer to FIG. 4). It is judged as to whether stirring for the corresponding particle reagent is required or not based on the reagent stirring information obtained from the analysis order and a program for avoiding carry-over between particle beads and, further, the stirring time is changed if necessary. Based on the result of judgement in the flow chart, the stirring timing and the dispensing timing of the liquid reagent in which fine particles are suspended are set. The set stirring timing and dispensing timing are stored in a memory device such as an IC memory or a magnetic memory device, and analysis is conducted under control for the operation of the dispensing probe and the stirrer based on the memory by a controller such as a microcomputer.

(1) According to this invention, reagent carry-over between the particle beads reagents in the reagent packs can be avoided. As a result, when analysis is conducted for the inspection item for which effect of the reagent carry-over is expected, analysis is made without suffering from the carry-over to prevent indication for false positive or erroneous result to make diagnosis reliable. Further, there is no requirement for re-inspection to mitigate the operation burdens of physicians and those concerned in the medical treatment, as well as reduce the cost for the operation.

(2) According to this invention, requirement for the stirring of plural particle beads reagents occurring within a single period can be coped with while not lowering the analysis performance and the inspection job can be made efficient without lowering the processing performance of the apparatus. Further, since the number of stirring operation cycles for the particle beads reagents can be reduced and, further, the number of cleaning cycles for the stirring rod or the stirrer can be decreased, the time and cost required therefor can be reduced and also decrease the cost during series of inspection operation such as for cleaning water and electric power. Further, it can also reduce the scattering and bubbling of the particle with reagents along beads stirring.

What is claimed is:

1. An immunological analyzing apparatus comprising:
   plural reagent vessels each for containing one of plural kinds of liquid reagents in which particles bonded with an antigen or an antibody are suspended;
   a stirring rod for stirring the liquid reagents in one of said plurality of reagent vessels,
   a probe for dispensing the liquid reagent in the one of the reagent vessels stirred by the stirring rod;
   a reaction vessel for mixing and reacting the liquid reagent received from the dispensing probe and a specimen to form a reaction mixture;
   a measuring device for measuring the reaction mixture in the reaction vessel; and
   means for determining whether or not the liquid reagent in the one of the reagent vessels is stirred prior to dispensing of the liquid reagent in the one of the reagent vessels to the reaction vessel, based on information regarding a predetermined period of stirring time and information regarding carry-over between the plural kinds of liquid reagents.

2. An immunological analyzing apparatus comprising:
   plural reagent vessels each containing one of plural kinds of liquid reagents in which particles bonded with an antigen or an antibody are suspended;
   a stirring vessel rod for stirring the liquid reagent in one of said plurality of reagent vessels,
   a probe for dispensing the liquid reagent in the one of the reagent vessels;
   a reaction vessel for mixing and reacting the liquid reagent received from the dispensing probe and a specimen to form a reaction mixture;
   a measuring device for measuring the reaction mixture in the reaction vessel; and
   means for determining a dispensing sequence of the liquid reagents in the reagent vessels to the reaction vessel and whether or not the one liquid reagent in the reagent vessels is to be stirred prior to dispensing of the one liquid reagent from the one of the reagent vessels to the reaction vessel, based on information regarding a predetermined period of stirring time and information regarding carry-over between each of the plural kinds of liquid reagents.

3. An immunological analyzing apparatus comprising:
   plural reagent vessels each containing one of plural kinds of liquid reagents in which particles bonded with an antigen or an antibody are suspended;
   a stirring rod for stirring the liquid reagent in one of said plurality of reagent vessels,
   a probe for dispensing the liquid reagent in the one of the reagent vessels;
   a reaction vessel for mixing and reacting the liquid reagent received from the dispensing probe and a specimen to form a reaction mixture;

a measuring device for measuring the reaction mixture in the reaction vessel; and means for determining timing of dispensing of the liquid reagent in the one of the reagent vessels to the reaction vessel based on information regarding a predetermined period of stirring time and information regarding carry-over between each of the plural kinds of liquid reagents.

4. An immunological analyzing method comprising:

dispensing from one of a plural kind of liquid reagents to one of a plurality of reagent vessels, a liquid reagent in which particles bonded with an antigen or antibody are suspended and mixing and reacting the liquid reagent with a specimen in a reaction vessel thereby analyzing the absence or presence of an antigen or an antibody in the specimen, including determining whether or not the liquid reagent in the reagent vessel is to be stirred prior to the dispensing of the liquid reagent in one of the reagent vessel to the reaction vessel based on information regarding a predetermined period of time of stirring and information regarding carry-over between each of the plural kinds of liquid reagents.

5. An immunological analyzing method, comprising:

dispensing liquid reagent from among plural kinds of liquid reagents in one of a plurality of reagent vessels in which particles bonded with an antigen or antibody are suspended and mixing and reacting the liquid reagent with the specimen in a reaction vessel thereby analyzing the absence or presence of an antigen or an antibody in the specimen, including:

determining a sequence for dispensing the liquid reagents in the one of the reagent vessels to the reaction vessel and whether or not stirring is to be conducted prior to the dispensing thereof based on information regarding a predetermined period of time of stirring and information regarding carry-over between each of the plural kinds of liquid reagents.

\* \* \* \* \*